(12) United States Patent
Naito

(10) Patent No.: US 8,058,474 B2
(45) Date of Patent: Nov. 15, 2011

(54) UREA DERIVATIVE AND PROCESS FOR PREPARING THE SAME

(75) Inventor: Toshihiko Naito, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/400,562

(22) Filed: Mar. 9, 2009

(65) Prior Publication Data

US 2009/0171112 A1 Jul. 2, 2009

Related U.S. Application Data

(62) Division of application No. 10/577,308, filed as application No. PCT/JP2004/016526 on Nov. 8, 2004, now Pat. No. 7,683,172.

(30) Foreign Application Priority Data

Nov. 11, 2003 (JP) ................. P2003-381249

(51) Int. Cl.
*C07C 275/32* (2006.01)
*C07C 271/58* (2006.01)

(52) U.S. Cl. .......................... 564/52; 560/29

(58) Field of Classification Search ............ 564/52; 560/29

See application file for complete search history.

(56) References Cited

U.S. PATENT DOCUMENTS

| | | | |
|---|---|---|---|
| 4,526,988 A | 7/1985 | Hertel | |
| 4,742,003 A | 5/1988 | Derynck et al. | |
| 4,764,454 A | 8/1988 | Ichijima et al. | |
| 5,180,818 A | 1/1993 | Cech et al. | |
| 5,464,826 A | 11/1995 | Grindey et al. | |
| 5,487,889 A | 1/1996 | Eckert et al. | |
| 5,553,037 A | 9/1996 | Tachibana | |
| 5,624,937 A | 4/1997 | Reel et al. | |
| 5,656,454 A | 8/1997 | Lee et al. | |
| 5,658,374 A | 8/1997 | Golver | |
| 5,733,913 A | 3/1998 | Blankley et al. | |
| 5,747,651 A | 5/1998 | Lemischka | |
| 5,750,376 A | 5/1998 | Weiss et al. | |
| 5,770,599 A | 6/1998 | Gibson | |
| 5,792,783 A | 8/1998 | Tang et al. | |
| 5,891,996 A | 4/1999 | Maten de Acosta del Rio et al. | |
| 6,143,764 A | 11/2000 | Kubo et al. | |
| 6,156,522 A | 12/2000 | Keay et al. | |
| 6,217,866 B1 | 4/2001 | Schlessinger et al. | |
| 6,346,398 B1 | 2/2002 | Pavco et al. | |
| 6,351,255 B1 | 2/2002 | Ishizuka et al. | |
| 6,476,040 B1 | 11/2002 | Norris et al. | |
| 6,524,583 B1 | 2/2003 | Thorpe et al. | |
| 6,534,535 B1 | 3/2003 | Zhu et al. | |
| 6,676,941 B2 | 1/2004 | Thorpe et al. | |
| 6,797,823 B1 | 9/2004 | Kubo et al. | |
| 6,811,779 B2 | 11/2004 | Rockwell et al. | |
| 6,821,987 B2 | 11/2004 | Kubo et al. | |
| 7,005,430 B2 | 2/2006 | Ueno et al. | |
| 7,135,466 B2 | 11/2006 | Sakai et al. | |
| 7,169,789 B2 | 1/2007 | Kubo et al. | |
| 7,253,286 B2 | 8/2007 | Funahashi et al. | |
| 7,435,590 B2 | 10/2008 | Komurasaki | |
| 7,547,703 B2 | 6/2009 | Roth et al. | |
| 7,612,092 B2* | 11/2009 | Funahashi et al. | 514/312 |
| 7,612,208 B2 | 11/2009 | Matsushima et al. | |
| 2002/0040127 A1 | 4/2002 | Jiang et al. | |
| 2003/0087907 A1 | 5/2003 | Kubo et al. | |
| 2003/0113713 A1 | 6/2003 | Glezer et al. | |
| 2003/0215523 A1 | 11/2003 | Ozawa et al. | |
| 2004/0009965 A1 | 1/2004 | Collins et al. | |

(Continued)

FOREIGN PATENT DOCUMENTS

EP 0405425 A2 1/1991

(Continued)

OTHER PUBLICATIONS

Nocka et al., "Expression of c-kit gene products in known cellular targets of W mutations in normal and W mutant mice-evidence for an impaired c-kit kinase in mutant mice," Genes & Development, vol. 3, pp. 816-826 (1989). XP-002522472.

(Continued)

*Primary Examiner* — Peter O Sullivan

(74) *Attorney, Agent, or Firm* — Birch, Stewart, Kolasch & Birch, LLP

(57) ABSTRACT

A process for preparing a compound (C) represented by the following formula:

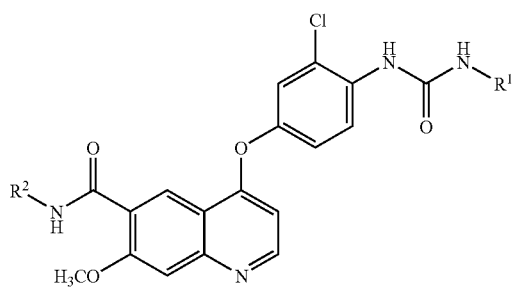

(C)

wherein $R^1$ represents hydrogen, $C_{1-6}$ alkyl or $C_{3-8}$ cycloalkyl, and $R^2$ represents hydrogen or methoxy, characterized by reacting a compound (A-1) represented by the following formula:

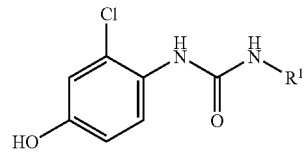

(A-1)

wherein $R^1$ has the same definition as above, with a compound (B) represented by the following formula:

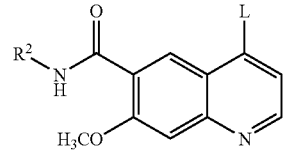

(B)

wherein $R^2$ has the same definition as above, and L represents a leaving group, is provided. Compound (C) is effective for prevention or treatment of various diseases associated with angiogenesis neoplasia.

5 Claims, No Drawings

U.S. PATENT DOCUMENTS

| | | |
|---|---|---|
| 2004/0034026 A1 | 2/2004 | Wood et al. |
| 2004/0053908 A1 | 3/2004 | Funahashi et al. |
| 2004/0132727 A1 | 7/2004 | Sakai et al. |
| 2004/0152759 A1 | 8/2004 | Abrams et al. |
| 2004/0191254 A1 | 9/2004 | Fagin |
| 2004/0242506 A1 | 12/2004 | Barges Causeret et al. |
| 2004/0253205 A1 | 12/2004 | Yamamoto et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0189629 A1 | 8/2006 | Bolger et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2008/0207617 A1 | 8/2008 | Miwa et al. |
| 2008/0214604 A1 | 9/2008 | Furitsu et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0209580 A1 | 8/2009 | Matsui |
| 2009/0247576 A1 | 10/2009 | Kamata |
| 2010/0105031 A1 | 4/2010 | Matsui et al. |

FOREIGN PATENT DOCUMENTS

| | | |
|---|---|---|
| EP | 0602851 A1 | 6/1994 |
| EP | 0684637 A2 | 11/1995 |
| EP | 0684820 | 12/1995 |
| EP | 0712863 A1 | 5/1996 |
| EP | 0795556 A1 | 9/1997 |
| EP | 0837063 A1 | 4/1998 |
| EP | 0870842 A2 | 10/1998 |
| EP | 0930305 A1 | 7/1999 |
| EP | 0930310 A1 | 7/1999 |
| EP | 1029853 A1 | 8/2000 |
| EP | 1153920 A1 | 11/2001 |
| EP | 0712863 B1 | 2/2002 |
| EP | 1 411 046 A1 | 4/2004 |
| EP | 1415987 A1 | 5/2004 |
| EP | 1 447 405 A1 | 8/2004 |
| EP | 1522540 A1 | 4/2005 |
| EP | 1535910 A1 | 6/2005 |
| EP | 1566379 A1 | 8/2005 |
| EP | 1604665 A1 | 12/2005 |
| EP | 1683785 A1 | 7/2006 |
| EP | 1 698 623 A1 | 9/2006 |
| EP | 1925676 A1 | 5/2007 |
| EP | 1 797 881 A1 | 6/2007 |
| EP | 1797877 A1 | 6/2007 |
| EP | 1859793 A1 | 11/2007 |
| EP | 1859797 A1 | 11/2007 |
| EP | 1894918 A1 | 3/2008 |
| EP | 1925941 A1 | 5/2008 |
| EP | 1949902 A1 | 7/2008 |
| EP | 1964837 A1 | 9/2008 |
| EP | 2 119 707 A1 | 11/2009 |
| GB | 2253848 A | 9/1992 |
| JP | 64-22874 A | 1/1989 |
| JP | 2-291295 A | 12/1990 |
| JP | 4-341454 A | 11/1992 |
| JP | 6-153952 A | 6/1994 |
| JP | 7-176103 A | 7/1995 |
| JP | 8-45927 A | 2/1996 |
| JP | 8-48078 A | 2/1996 |
| JP | 9-23885 A | 1/1997 |
| JP | 9-234074 A | 9/1997 |
| JP | 63-28427 A | 2/1998 |
| JP | 11-501343 A | 2/1999 |
| JP | 11-143429 A | 5/1999 |
| JP | 11-158149 A | 6/1999 |
| JP | 11-322596 A | 11/1999 |
| JP | 3040486 A | 5/2000 |
| JP | 3088018 A | 9/2000 |
| JP | 2000-328080 A | 11/2000 |
| JP | 2001-131071 A | 5/2001 |
| JP | 2002-3365 A | 1/2002 |
| JP | 2002-114710 A | 4/2002 |
| JP | 2002-536414 A | 10/2002 |
| JP | 2003-12668 A | 1/2003 |
| JP | 2003-26576 A | 1/2003 |
| JP | 3420549 B2 | 6/2003 |
| JP | 2003-525595 A | 9/2003 |
| JP | 2004-513964 A | 5/2004 |
| JP | 2004-155773 A | 6/2004 |
| JP | 2004-531549 A | 10/2004 |
| JP | 2005-501074 A | 1/2005 |
| JP | 2005-504111 A | 2/2005 |
| JP | 2005-520834 A | 7/2005 |
| JP | 3712393 B2 | 8/2005 |
| JP | 2006-508981 A | 3/2006 |
| JP | 2006-515884 A | 6/2006 |
| WO | WO 92/20642 A1 | 11/1992 |
| WO | WO 95/15758 A1 | 6/1995 |
| WO | WO 95/17181 A1 | 6/1995 |
| WO | WO 95/19774 A1 | 7/1995 |
| WO | WO 96/09294 A1 | 3/1996 |
| WO | WO 96/26997 A1 | 9/1996 |
| WO | WO 96/30347 A1 | 10/1996 |
| WO | WO 96/33980 A1 | 10/1996 |
| WO | WO 96/39145 A1 | 12/1996 |
| WO | WO 96/40142 A1 | 12/1996 |
| WO | WO 97/03069 A1 | 1/1997 |
| WO | WO 97/13760 A1 | 4/1997 |
| WO | WO 97/13771 A1 | 4/1997 |
| WO | WO-97/17329 A1 | 5/1997 |
| WO | WO 97/21437 A1 | 6/1997 |
| WO | WO 97/38984 A1 | 10/1997 |
| WO | WO 97/48693 A1 | 12/1997 |
| WO | WO-98/00134 A1 | 1/1998 |
| WO | WO 98/02434 A1 | 1/1998 |
| WO | WO 98/02437 A1 | 1/1998 |
| WO | WO 98/02438 A1 | 1/1998 |
| WO | WO 98/13350 A1 | 4/1998 |
| WO | WO 98/14437 A1 | 4/1998 |
| WO | WO 98/23613 A1 | 6/1998 |
| WO | WO 98/32436 A1 | 7/1998 |
| WO | WO 98/35958 A1 | 8/1998 |
| WO | WO 98/37079 A1 | 8/1998 |
| WO | WO 98/50346 A2 | 11/1998 |
| WO | WO 98/52558 A1 | 11/1998 |
| WO | WO 99/00357 A1 | 1/1999 |
| WO | WO-99/32106 A1 | 7/1999 |
| WO | WO 99/32110 A1 | 7/1999 |
| WO | WO 99/32111 A1 | 7/1999 |
| WO | WO-99/32436 A1 | 7/1999 |
| WO | WO 99/35132 A1 | 7/1999 |
| WO | WO 99/35146 A1 | 7/1999 |
| WO | WO 99/43654 A1 | 9/1999 |
| WO | WO 99/62890 A1 | 12/1999 |
| WO | WO 00/31048 A1 | 6/2000 |
| WO | WO-00/42012 A1 | 7/2000 |
| WO | WO-00/43366 A1 | 7/2000 |
| WO | WO 00/43384 A1 | 7/2000 |
| WO | WO 00/44728 A1 | 8/2000 |
| WO | WO 00/47212 A1 | 8/2000 |
| WO | WO 00/50405 A1 | 8/2000 |
| WO | WO 01/02369 A2 | 1/2001 |
| WO | WO 01/23375 A1 | 4/2001 |
| WO | WO 01/27081 A1 | 4/2001 |
| WO | WO 01/32926 A2 | 5/2001 |
| WO | WO 01/36403 A1 | 5/2001 |
| WO | WO 01/40217 A1 | 6/2001 |
| WO | WO-01/45689 A2 | 6/2001 |
| WO | WO 01/47890 A1 | 7/2001 |
| WO | WO 01/47931 A1 | 7/2001 |

| | | |
|---|---|---|
| WO | WO 01/60814 A2 | 8/2001 |
| WO | WO 02/16348 A1 | 2/2002 |
| WO | WO-02/32872 A1 | 4/2002 |
| WO | WO 02/36117 A1 | 5/2002 |
| WO | WO 02/41882 A2 | 5/2002 |
| WO | 02/44156 A2 | 6/2002 |
| WO | 02/44156 A3 | 6/2002 |
| WO | WO-02/072578 A2 | 9/2002 |
| WO | WO 02/080975 A1 | 10/2002 |
| WO | WO 00/71097 A1 | 11/2002 |
| WO | WO 02/088110 A1 | 11/2002 |
| WO | WO 02/092091 A1 | 11/2002 |
| WO | WO 03/006462 A1 | 1/2003 |
| WO | WO 03/013529 A1 | 2/2003 |
| WO | WO 03/027102 A1 | 4/2003 |
| WO | WO 03/028711 A2 | 4/2003 |
| WO | WO 03/033472 A1 | 4/2003 |
| WO | WO 03/050090 A1 | 6/2003 |
| WO | WO 03/074045 A1 | 9/2003 |
| WO | WO 03/079020 A2 | 9/2003 |
| WO | WO 2004/006862 A2 | 1/2004 |
| WO | WO 2004/020434 A1 | 3/2004 |
| WO | WO 2004/032872 A2 | 4/2004 |
| WO | WO 2004/032937 A1 | 4/2004 |
| WO | WO 2004/035052 A1 | 4/2004 |
| WO | WO 2004/039785 A1 | 5/2004 |
| WO | WO 2004/041308 A1 | 5/2004 |
| WO | WO 2004/043472 A1 | 5/2004 |
| WO | WO-2004/064730 A2 | 8/2004 |
| WO | WO 2004/078144 A2 | 9/2004 |
| WO | WO-2004/080462 A1 | 9/2004 |
| WO | WO-2004/080966 A1 | 9/2004 |
| WO | WO-2004/101526 A1 | 11/2004 |
| WO | WO 2005/027972 A2 | 3/2005 |
| WO | WO 2005/030140 A2 | 4/2005 |
| WO | WO 2005/044788 A1 | 5/2005 |
| WO | WO 2005/051366 A2 | 6/2005 |
| WO | WO 2005/056764 A2 | 6/2005 |
| WO | WO-2005/063713 A1 | 7/2005 |
| WO | WO 2005/082854 A1 | 9/2005 |
| WO | WO 2005/092896 A1 | 10/2005 |
| WO | WO 2005/117887 A1 | 12/2005 |
| WO | WO-2006/030826 A1 | 3/2006 |
| WO | WO 2006/030941 A1 | 3/2006 |
| WO | WO 2006/030947 A1 | 3/2006 |
| WO | WO 2006/036941 A2 | 4/2006 |
| WO | WO 2006/062984 A2 | 6/2006 |
| WO | WO 2006/090930 A1 | 8/2006 |
| WO | WO 2006/090931 A1 | 8/2006 |
| WO | WO 2006/137474 A1 | 12/2006 |
| WO | WO 2007/014335 A | 2/2007 |
| WO | WO 2007/015569 A1 | 2/2007 |
| WO | WO 2007/015578 A1 | 2/2007 |
| WO | WO 2007/040565 A2 | 4/2007 |
| WO | WO 2007/052849 A1 | 5/2007 |
| WO | WO 2007/052850 A1 | 5/2007 |
| WO | WO 2007/061127 A1 | 5/2007 |
| WO | WO 2007/0611330 A1 | 5/2007 |
| WO | WO 2007/136103 A1 | 11/2007 |

OTHER PUBLICATIONS

Li et al., "Abrogation of c-kit/Steel factor-dependent Tumorigenesis by Kinase Defective Mutants of the c-kit Receptor: c-kit Kinase Defective Mutants as Candidate Tools for Cancer Gene Therapy," Cancer Research, vol. 56, pp. 4343-4346 (1996). XP-002522473.
CancerCare, www.lungcancer.org/reading/types/php, 2009.
U.S. Office Action issued in U.S. Appl. No. 10/797,903 Aug. 20, 2009.
Abuzar et al., "Synthesis of some new 7-chloro-4-substituted quinolines as potential antiparasitic agents (1)", Eur. J. Med. Chem., vol. 21, No. 1, pp. 5-8 (1986).
Gardner, G. et al., Pesticide Biochemistry and Physiology, 1985, vol. 24, No. 3, pp. 285 to 297.
Nugiel, D.A., et al., Journal of Medicinal Chemistry, 2002, vol. 45, No. 24, pp. 5224 to 5232.
Proceedings of the American Association for Cancer Research, vol. 45, Mar. 2004, pp. 1070-1071.
Gall-Istok et al., STN Accession No. 99:88018, Abstract of Acta Chimica Hungarica, 1983, vol. 112, No. 2, 241-247 (Abstract Only).
Cairns et al., "New antiallergic pyrano[3,2-g]quinoline-2,8-dicarboxylic acids with potential for the topical treatment of asthma", Journal of Medicinal Chemistry, 1985, vol. 28, pp. 1832-1842.
European Patent Office Search Report, Appl. No. 06768437.3, Oct. 11, 2010, pp. 1-10.
Hennequin, L. F. et al, "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 2002, vol. 45, pp. 1300-1312.
Traxler, P. et al, "AEE788: A Dual Family Epidermal Growth Factor Receptor/ErbB2 and Vascular Endothelial Growth Factor Receptor Tyrosine Kinase Inhibitor with Antitumor and Antiangiogenic Activity," Cancer Research, Jul. 15, 2004, vol. 64, pp. 4931-4941.
USPTO Office Action, U.S. Appl. No. 11/997,719, Sep. 3, 2010, pp. 1-10.
EPO Supplementary European Search Report, Appl. No. 06833681.7, Nov. 24, 2010, pp. 1-15.
Juurikivi, A., et al, "Inhibition of c-kit tyrosine kinase by imatinib mesylate induces apoptosis in mast cells in rheumatoid synovia: a potential approach to the treatment of arthritis," Ann Rheum Dis, 2005, vol. 64, pp. 1126-1131.
USPTO Office Action, U.S. Appl. No. 12/092,539, Jan. 7, 2011, pp. 1-12.
Vippagunta, S. R. et al, "Crystalline solids," Advanced Drug Delivery Reviews, 2001, vol. 48, pp. 3-26.
Yamada et al., "New Technique for Staining," Monthly Medical Technology Supplementary Volume, Apr. 1999.
US Office Action dated Feb. 23, 2011 for U.S. Appl. No. 11/997,543.
Zhang et al., "Overexpression of Platelet-Derived Growth Factor Receptor α in Endothelial Cells of Hepatocellular Carcinoma Associated with High Metastatic Potential", Clin Cancer Res, pp. 8557-8563, Nov. 2005.
Extended European Search Report, dated Jan. 19, 2011, for European Application No. 07806561.2.
Anderson, et al., "Preparation of Water-soluble Compounds through Salt Formation, The Practice of Medicinal Chemistry", Technomics, pp. 347-349 and pp. 355-356, Sep. 25, 1999.
Japanese Office Action for Application No. P2005-516605, dated Jun. 1, 2010.
Bellone et al., "Growth stimulation of colorectal carcinoma cells via the c-kit receptor is inhibited by TGF-beta1," J. Cell. Physiol., vol. 172, pp. 1-11, 1997.
Berdel et al., "Recombinant Human Stem Cell Factor Stimulates Growth of a Human Glioblastoma Cell Line Expressing c-kit Protooncogene," Cancer Research, vol. 52, pp. 3498-3502, Jun. 15, 1992.
Blume-Jensen et al., "Activation of the human c-kit product by ligand-induced dimerization mediates circular actin reorganization and chemotaxis," EMBO J., vol. 10, No. 13, pp. 4121-4128, 1991.
Boissan et al., "c-Kit and c-kit mutations in mastocytosis and other hematological diseases," J. Leukoc. Biol., vol. 67, pp. 135-148, Feb. 2000.
Bussolino et al., "Role of Soluble Mediators in Angiogenesis," Eur. J. Cancer, vol. 32A, No. 14, pp. 2401-2412, 1996.
Chinese Office Action for Application No. 200580026468.7 dated Jun. 26, 2009.
Chinese Office Action for Application No. 200710007097.9 dated Mar. 6, 2009.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, vol. 98. No. 3, pp. 463-469, Mar. 20, 2002.
Clark et al., "Safety and Pharmacokinetics of the Dual Action Raf Kinase and Vascular Endothelial Growth Factor Receptor Inhibitor, BAY 43/9006, in Patients with Advanced, Refractory Solid Tumors," Clin. Cancer Res., vol. 11, No. 15, pp. 5472-5480, Aug. 1, 2005.
Cohen et al., "Expression of Stem Cell Factor and c-kit in Human Neuroblastoma," Blood, vol. 84, No. 10, pp. 3465-3472, Nov. 15, 1994.

Croom et al., "Imatinib Mesylate; In the Treatment of Gastrointestinal Stromal Tumours," Drugs, vol. 63, No. 5, pp. 513-522, 2003.

Deplanque et al., "Anti-angiogenic agents: clinical trial design and therapies in development," Eur. J. Cancer, vol. 36, pp. 1713-1724, 2000.

Dermer, "Another Anniversary for the War on Cancer," Biotechnology, vol. 12, pp. 320, Mar. 12, 1994.

European Office Action for Application No. 04025700.8 dated Apr. 10, 2006.

Extended European Search Report for Application No. 06832529.9 dated Jul. 29, 2009.

Folkman et al., "Angiogenesis," J. Biol. Chem., vol. 267, No. 16, pp. 10931-10934, Jun. 5, 1992.

Folkman et al., "Clinical Applications of Research on Angiogenesis", New Eng. J. Med., vol. 333, pp. 1757-1763, 1995.

Folkman, "New Perspectives in Clinical Oncology from Angiogenesis Research," Eur. J. Cancer, vol. 32A, No. 14, pp. 2534-2539, 1996.

Folkman, "What Is the Evidence That Tumors Are Angiogenesis Dependent?," J. Natl. Cancer Inst., vol. 82, No. 1, pp. 4-6, Jan. 3, 1990.

Freshney, Culture of Animal Cells: A Manual of Basic Technique, Alan R. Liss, New York, pp. 3-4, 1983.

Furitsu et al., "Stable medicinal compositions of quinolinecarboxamide derivative", Database CAPLUS Abstract, Columbus, Ohio, US, 2006.

Furitsu et al., "Identification of Mutations in the Coding Sequence of the Proto-Oncogene c-kit in a Human Mast Cell Leukemia Cell Line Causing Ligand-Independent Activation of c-kit Product", J. Clin. Invest., vol. 92, pp. 1736-1744, 1993.

Furuta et al., "Synthesis and Biological Evaluation of Selective Inhibitors of PDGF Receptor Auto Phosphorylation," Abstract No. 64, Pharmaceutical Research Laboratories, Kirin Brewery Co., Ltd. Takasaki, Gunma, Japan, 226th ACS National Meeting, New York, NY, Sep. 7-11, 2003.

Golkar et al., "Mastocytosis," Lancet, vol. 349, pp. 1379-1385, May 10, 1997.

Haleblian, "Characterization of Habits and Crystalline Modification of Solids and Their Pharmaceutical Applications," J. Pharma. Sci., vol. 64, No. 8, pp. 1269-1288, Aug. 1975.

Hamel et al., "The road less travelled: c-kit and stem cell factor," J. Neurooncol., vol. 35, pp. 327-333, 1997.

Hayek et al., "A in vivo model for study of the angiogenic effects of basic fibroblast growth factor," Biochem. Biophys. Res. Commun., vol. 147, No. 2, pp. 876-880, Sep. 15, 1987.

Heinrich et al., "Inhibition of c-kit receptor tyrosine kinase activity by STI 571, a selective tyrosine kinase inhibitor," Blood, vol. 96, No. 3, pp. 925-932, Aug. 1, 2000.

Heinrich et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.

HIBI et al., "Coexpression of the stem cell factor and the c-kit genes in small-cell lung cancer," Oncogene, vol. 6, pp. 2291-2296, 1991.

Hines et al., "Coexpression of the c-kit and Stem Cell Factor Genes in Breast Carcinomas," Cell Growth Differ., vol. 6, pp. 769-779, Jun. 1995.

Hogaboam et al., "Novel Role of Transmembrane SCF for Mast Cell Activation and Eotaxin Production in Mast Cell-Fibroblast Interactions," J. Immunol., vol. 160, pp. 6166-6171, 1998.

Ikeda et al., "Changes in phenotype and proliferative potential of human acute myeloblastic leukemia cells in culture with stem cell factor," Exp. Hematol., vol. 21, pp. 1686-1694, 1993.

Ikeda et al., "Expression and Functional Role of the Proto-oncogene c-kit in Acute Myeloblastic Leukemia Cells," Blood, vol. 78, No. 11, pp. 2962-2968, Dec. 1, 1991.

International Preliminary Report on Patentability and Written Opinion of the International Searching Authority for Application No. PCT/JP2004/003087 dated on Feb. 13, 2006.

International Preliminary Report on Patentability and Written Opinion of the International Searching Authority for Application No. PCT/JP2006/312487 dated Dec. 24, 2007.

International Search Report for Application No. PCT/JP01/09221 dated Jan. 15, 2002.

International Search Report for Application No. PCT/JP2004/003087 dated Jul. 13, 2004.

Jakeman et al., "Developmental expression of binding sites and messenger ribonucleic acid for vascular endothelial growth factor suggests a role for this protein in vasculogenesis and angiogenesis," Endocrinology, vol. 133, No. 2, pp. 848-859, Aug. 1993.

Japanese Notice of Allowance for Application No. 2005-515330 dated Apr. 21, 2009.

Kanakura et al., "Expression, Function and Activation of The Procto-oncogene c-Kit Product in Human Leukemia Cells," Leuk. Lymphoma, vol. 10, pp. 35-41, 1993.

Kay et al., "Eosinophils and Eosinophil-Associated Cytokines in Allergic Inflammation," Int. Arch. Allergy Immunol., vol. 113, pp. 196-199, 1997.

Kitamura at al., "Regulation of Development, Survival and Neoplastic Growth of Mast Cells through the c-kit Receptor," Int. Arch. Allergy. Immunol. vol. 107, pp. 54-56, 1995.

Kolibaba et al., "Protein tyrosine kinases and cancer," Biochem. Biophys. Acta., vol. 1333, pp. F217-F248, 1997.

Korean Office Action for Application No. 10-2007-7013993 dated Jul. 31, 2007.

Kotva et al., "Substances with Antineoplastic Activity, LIII. N-{d-(4-Pyrrolo[2,3-d]Pyrimidinylthio)Valery} Amino Acids and Analogous Derivatives of Di- and Triglycine," Collection Czechoslov. Chem. Commun., vol. 38, pp. 1438-1444. 1973.

Lasota et al., "Mutations in Exons 9 and 13 of KIT Gene Are Rare Events in Gastrointestinal Stromal Tumors: A Study of 200 Cases," Am. J. Pathol., vol. 157, No. 4, pp. 1091-1095, Oct. 2000.

Lev et al., "A specific combination of substrates is involved in signal transduction by the kit-encoded receptor," EMBO J., vol. 10, No. 3, pp. 647-654, 1991.

Longley et al., "Altered Metabolism of Mast-Cell Growth Factor (c-kit Ligand) in Cutaneous Mastocytosis," N. Engl. J. Med., vol. 328, pp. 1302-1307, May 6, 1993.

Longley et al., "Classes of c-KIT activating mutations: proposed mechanisms of action and implications for disease classification and therapy," Leukemia Res., vol. 25, pp. 571-576, 2001.

Longley et al., "Somatic c-KIT activating mutation in urticaria pigmentosa and aggressive mastocytosis: establishment of clonality in a human mast cell neoplasm," Nat. Genet., vol. 12, pp. 312-314, Mar. 1996.

Lukacs et al., "Stem cell factor (c-kit ligand) influences eosinophil recruitment and histamine levels in allergic airway inflammation," J. Immunol., vol. 156, pp. 3945-3951, May 1996.

Matsui et al., "E7080(ER-203492-00), a Novel VEGF Receptor Tyrosine Kinase Inhibitor-I. Characterization as an Angiogenesis Inhibitor," Abstract# 51, AACR, Washington, DC, Jul. 11-14, 2003.

Matsui et al., "E7080, a novel multi-receptor Tyrosine Kinases Inhibitor, inhibited in vitro / in vivo VEGF-and SCF-driven angiogenesis in SCLC cell line," Abstract #146, EORTC-NCI-AACR, Geneva, Switzerland, Sep. 28-Oct. 1, 2004.

Matsui et al., "Quantitative analysis of the profile of tumor vessels may be useful as predictive biomarkers for E7080, a KDR Tyrosine Kinase Inhibitor," Abstract #4631, 98th AACR Annual Meeting, Los Angeles, CA, Apr. 14-18, 2007.

Matsui et al., "VEGFRs inhibitor E7080 inhibits lymph node metastasis of human breast carcinoma, by preventing murine lymphatic endothelial cells from lymphangiogenesis," Abstract # PD12-8, 18th EORTC-NCI-AACR Symposium on "Molecular Targets and Cancer Therapeutics", Prague, Czech republic, Nov. 7-10, 2006.

Matsui et al., "E7080, a novel inhibitor that targets multiple kinases has potent antitumor activities against stem cell factor producting human small cell lung cancer, H146, based on angiogenesis inhibition", International J. Cancer, vol. 122, pp. 664-671, 2008.

Meltzer, "The pharmacological basis for the treatment of perennial allergic rhinitis and non-allergic rhinitis with topical corticosteroids," Allergy, vol. 52, Suppl. 36, pp. 33-40, 1997.

Mendel et al., "In Vivo Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship," Clin. Cancer Res., vol. 9, pp. 327-337, Jan. 2003.
Metcalf, "Lineage commitment in the progeny of murine hematopoietic preprogenitor cells: Influence of thrombopoietin and interleukin 5," Proc. Natl. Acad. Sci. USA, vol. 95, pp. 6408-6412, May 1998.
Metcalfe et al., "Mast Cells," Physiological Reviews, vol. 77, No. 4, pp. 1033-1079, Oct. 1997.
Metcalfe, "Classification and Diagnosis of Mastocytosis: Current Status," J. Invest. Dermatol., vol. 96, pp. 2S-4S, 1991.
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," Abstract B-15, AIMECS 03, Kyoto, Japan, Oct. 14-17, 2003.
Myers et al., "The Preparation and SAR of 4-(Anilino), 4-(Phenoxy), and 4-(Thiophenoxy)-Quinazolines: Inhibitors of p56Ick and EGF-R Tyrosine Kinase Activity," Bioorg. Med. Chem. Letts., vol. 7, No. 4, pp. 417-420, 1997.
Naclerio et al., "Rhinitis and Inhalant Allergens," JAMA, vol. 278, No. 22, pp. 1842-1848, Dec. 10, 1997.
Nagata et al., "Elevated expression of the proto-oncogene c-kit in patients with mastocytosis," Leukemia, vol. 12, pp. 175-181, 1998.
Nakamura et al., "E7080(ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract # 52, AACR, Washington, DC, Jul. 11-14, 2003.
Naruse et al., "Antitumor activity of the slective epidermal growth factor receptor-tyrosine kinase inhibitor (EGFR-TKI) IRESSA (ZD1839) in an EGFR-expressing multidrug-resistant cell line in vitro and in vivo," Int. J. Cancer, vol. 98, No. 2, pp. 310-315, 2002.
Natali et al., "Breast Cancer is Associated with Loss of the c-kit Oncogene Product," Int. J. Cancer, vol. 52, pp. 713-717, 1992.
NCBI GeneBank Accession No. NM_000222, Feb. 11, 2008.
Okayama et al., "Activation of Eosinophils with Cytokines Produced by Lung Mast Cells," Int. Arch. Allergy Immunol., vol. 114, Suppl. 1, pp. 75-77, 1997.
Okayama et al., "Human Lung Mast Cells are Enriched in the Capacity to Produce Granulocyte-Macrophage Colony-Stimulating Factor in Response to IgE-Dependent Stimulation", Eur. J. Immunol., vol. 28, pp. 708-715, 1998.
Redefining the Frontiers of Science 94th Annual Meeting, American Association for Cancer Research, vol. 44, 2nd Edition, Washington, DC, pp. 10-11, Jul. 11-14, 2003.
Scheijen et al., "Tyrosine kinase oncogenes in normal hematopoiesis and hematological disease," Oncogene, vol. 21, pp. 3314-3333, 2002.
Sekido et al., "Preferential Expression of c-kit Protooncogene Transcripts in Small Cell Lung Cancer," Cancer Res., vol. 51, pp. 2416-2419, May 1, 1991.
Spacey et al., "Indolocarbazoles: Potent and Selective Inhibitors of Platelet-Derived Growth Factor Receptor Autophosphorylation," Biochem. Pharmacol., vol. 55, pp. 261-271, 1998.
Strohmeyer et al., "Expression of the hst-1 and c-kit Protooncogenes in Human Testicular Germ Cell Tumors," Cancer Res., vol. 51, pp. 1811-1816, Apr. 1, 1991.
Supplementary European Search Report for Application No. 04719054.1 dated Apr. 17, 2009.
Supplementary European Search Report for Application No. 04818213.3 dated Jul. 30, 2007.
Taguchi et al., "A novel orally active inhibitor of VEGF receptor tyrosine kinases KRN951: Anti-angiogenic and anti-tumor activity against human solid tumors," Proc. Amer. Assoc. Cancer Res., vol. 45, pp. 595-596, Mar. 2004.
Taniguchi et al., "Effect of c-kit Mutation on Prognosis of Gastrointestinal Stromal Tumors," Cancer Res., vol. 59, pp. 4297-4300, Sep. 1, 1999.
Thomas et al., "The Eosinophil and its Role in Asthma," Gen. Pharmac., vol. 27, No. 4, pp. 593-597, 1996.
Tian et al., "Activating c-Kit Gene Mutations in Human Germ Cell Tumors," Am. J. Pathol., vol. 154, No. 6, pp. 1643-1647, Jun. 1999.
Tonary et al., "Lack of Expression of c-Kit is Ovarian Cancers is Associated with Poor Progonosis," Int. J. Cancer (Pred. Oncol.), vol. 89, pp. 242-250, 2000.
U.S Office Action dated May 3, 2010 for U.S. Appl. No. 11/662,425, filed Apr. 4, 2008.
U.S. Office Action dated Dec. 11, 2007 for U.S. Appl. No. 10/797,903, filed Mar. 10, 2004.
U.S. Office Action dated Feb. 9, 2009 for U.S. Appl. No. 11/347,749, filed Feb. 3, 2006.
U.S. Office Action issued in U.S. Appl. No. 10/577,531, issued on Sep. 23, 2008.
Wakeling et al., "ZD1839 (Iressa): An Orally Active Inhibitor of Epidermal Growth Factor Signaling with Potential for Cancer Therapy," Cancer Res., vol. 62, pp. 5749-5753, Oct. 15, 2002.
Wang et al., "The Expression of the Proto-Oncogene C-Kit in the Blast Cells of Acute Myeloblastic Leukemia," Leukemia, vol. 3, No. 10, pp. 699-702, Oct. 1989.
Wang et al., "A Convenient Set of Bidentate Pyridine Ligands for Combinatorial Synthesis", Tetrahedron Lett., vol. 40, pp. 4779-4782, 1999.
Wedge et al., "AZD2171: A Highly Potent, Orally Bioavailable, Vascular Endothelial Growth Factor Receptor-2 Tyrosine Kinase Inhibitor for the Treatment of Cancer," Cancer Res., vol. 65, No. 10, pp. 4389-4400, May 15, 2005.
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract # 50, AACR, Washington, DC, Jul. 11-14, 2003.
Yamamoto et al., "E7080 a novel multitargeted tyrosine kinase inhibitor, has direct anti-tumor efficacy via inhibition of KIT signaling in small cell lung cancer," Abstract #4636, AACR, Orlando, FL, Mar. 27-31, 2004.
Yamamoto et al., "E7080, an oral multi-targeted tyrosine kinase inhibitor has direct anti-tumor efficacy via inhibition of KIT signaling in gastrointestinal stromal tumor (GIST)," Abstract #4038, 97th annual meeting AACR, Washington, DC, Apr. 1-5, 2006.
"Asu no Shinyaku" ("The New Drugs of Tomorrow"), Update Summary, Dec. 2006, ISSN 1343-4462, pp. 81-83.
Agarwal et al., "Binding of Discoidin Domain Receptor 2 to Collagen I: An Atomic Force Microscopy Investigation," Biochemistry, vol. 41, pp. 11091-11098, 2002.
Alvares Da Silva et al., "A Novel Germ-Line Point Mutation in RET Exon 8 (Gly533Cys) in a Large Kindred with Familiar Medullary Thyroid Carcinoma", The Journal of Clinical Endocrinology & Metabolism, vol. 88, No. 11, 2003, pp. 5438-5443.
Baker et al., "Blockade of Vascular Endothelial Growth Factor Receptor and Epidermal Growth Factor Receptor Signaling for Therapy of Metastatic Human Pancreatic Cancer," Cancer Research, vol. 62, pp. 1996-2003, Apr. 1, 2002.
Benjamin et al., "Selective Ablation of Immature Blood Vessels in Estabished Human Tumors Follows Vascular Endothelial Growth Factor Withdrawal", The Journal of Clinical Investigation, vol. 103, No. 2, Jan. 1999, p. 159-165.
Bergers et al., "Benefits of Targeting Both Pericytes and Endothelial Cells in the Tumor and Vasculature with Kinase Inhibitors", The Journal of Clinical Investigtion, vol. 111, No. 9, May 2003, pp. 1287-1295.
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer, vol. 102, 2002, pp. 101-108.
Cappellen et al., "Frequent Activating Mutations of FGFR3 in Human Bladder and Cervix Carcinomas," Nature Genetics, vol. 23, Sep. 1999, pp. 18-20.
Carlomagno et al., "BAY 43-9006 Inhibition of Oncogenic RET Mutants", Journal of the National Cancer Institute, vol. 98, No. 5, Mar. 1, 2006, pp. 326-334.
Carlomagno et al., "ZD6474, an Orally Available Inhibitor of KDR Tyrosine Kinase Acrivity, Efficiently Blocks Oncogenic RET Kinases," Cancer Research, vol. 62, pp. 7284-7290, Dec. 15, 2002.

Chen et al., "FGFR3 as a Therapeutic Target of the Small Molecule Inhibitor PKC412 in Hematopoietic Malignancies", Oncogene, vol. 24, 2005, pp. 8259-8267.

Chesi et al., "Activated fibroblast growth factor receptor 3 is an oncogene that contributes to tumor progression in multiple myeloma," Blood, vol. 97, No. 3, pp. 729-736, Feb. 1, 2001.

Chesi et al., "Frequent Translocation t(4;14)(p16.3:q32.3) in Multiple Myeloma is Associated with Increased Expression and Activating Mutations of Fibroblast Growth Factor Receptor 3", Nature Genetics, vol. 16, Jul. 1997, pp. 260-264.

Elisei et al., "Identification of a Novel Point Mutation in the RET Gene (Ala883Thr), Which is Associated with Medullary Thyroid Carcinoma Phenotype Only in Homozygous Condition", The Journal of Clinical Endocrinology & Metabolism, vol. 89, No. 11, 2004, pp. 5823-5827.

Erber et al., "Combined Inhibition of VEGF- and PDGF-Signaling Enforces Tumor Vessel Regression by Interfering with Pericyte-mediated Endothelial Cell Survival Mechanisms", FASEB Journal, vol. 18, No. 2, 2004, pp. 338-340, XP-002548466.

European Office Action for European Application No. 04719054.1, dated Oct. 30, 2009.

Extended European Search Report for European Application No. 06782407.8 dated Jul. 23, 2010.

Gatzemeier et al., "Phase III Comparative Study of High-Dose Cisplatin Versus a Combination of Paclitaxel and Cisplatin in Patients with Advanced Non-Small-Cell Lung Cancer", Journal of Clinical Oncology, vol. 18, No. 19, pp. 3390-3399, Oct. 1, 2000.

Giles, "The Vascular Endothelial Growth Factor (VEGF) Signaling Pathway: A Therapeutic Target in Patients with Hematologic Malignancies", The Oncologist, vol. 6, Suppl. 5, 2001, pp. 32-39.

Haller, "Chemotherapy for Advanced Pancreatic Cancer", Int. J. Radiation Oncology Biol. Phys., vol. 56, No. 4, Supplement, 2003, pp. 16-23.

Hattori et al., "Immunohistochemical Detection of K-sam Protein in Stomach Cancer", Clinical Cancer Research, vol. 2, No. 8, Aug. 1996, pp. 1373-1381.

Haymo et al., "Pericytes in Experimental MDA-MB231 Tumor Angiogenesis", Histochemistry and Cell Biology, vol. 117, No. 6, Jun. 2002, pp. 527-534.

Hurwitz et al., "Bevacizumab Plus Irinotecan, Fluorouracil, and Leucovorin for Metastatic Colorectal Cancer", The New England Journal of Medicine, vol. 350, No. 23, Jun. 3, 2004, pp. 2335-2342.

Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts," American Journal of Pathology, vol. 165, No. 1, pp. 35-52, Jul. 2004.

Inoue et al., "Molecular Target Therapy Targeting Angiogenesis Pathways", The Nishinihon Journal of Urology, vol. 66, 2004, pp. 425-432.

International Search Report for Application No. PCT/JP2006/322514, dated Jan. 23, 2007.

International Search Report for Application No. PCT/JP2006/323881, dated Jan. 23, 2007.

International Search Report for Application No. PCT/JP2007/060560, dated Sep. 11, 2007.

International Search Report for Application No. PCT/JP2007/063525, dated Sep. 4, 2007.

International Search Report for Application No. PCT/JP2007/067088, dated Nov. 20, 2007.

International Search Report for Application No. PCT/JP2008/051024, dated Apr. 1, 2008.

International Search Report for Application No. PCT/JP2008/051697, dated Mar. 4, 2008.

International Search Report for Application No. PCT/JP2008/070321, dated Jan. 20, 2009.

International Search Report for Application No. PCT/JP2009/051244, dated Mar. 24, 2009.

International Search Report for Application No. PCT/JP2010/063804, dated Sep. 14, 2010.

International Search Report for Application No. PCTJP2006/315698, dated Oct. 17, 2006.

International Search Report for Application PCT/JP2006/315563, dated Sep. 5, 2006.

Itoh et al., "Preferential Alternative Splicing in Cancer Generates a K-sam Messenger RNA with Higher Transforming Activity," Cancer Research, vol. 54, pp. 3237-3241, Jun. 15, 1994.

Jhiang, "The RET Proto-Oncogene in Human Cancers", Oncogene, vol. 19, 2000, pp. 5590-5597.

Jiminez et al., "Pheochromocytoma and Medullary Thyroid Carcinoma: A New Genotype-Phenotype Correlation of the RET Protooncogene 891 Germline Mutation", The Journal of Clinical Endocrinology & Metabolism, vol. 89, No. 8, 2004, pp. 4142-4145.

Johnson et al., "Paclitaxel Plus Carboplatin in Advanced Non-Small-Cell Lung Cancer: A Phase II Trial", Journal of Clinical Oncology, vol. 14, No. 7, Jul. 1996, pp. 2054-2060.

Jung et al., "Effects of Combination Anti-Vascular Endothelial Growth Factor Receptor and Anti-Epidermal Growth Factor Receptor Therapies on the Growth of Gastric Cancer in a Nude Mouse Model", European Journal of Cancer, vol. 38, 2002, pp. 1133-1140.

Kashuk et al., "Phenotype-Genotype Correlation in Hirschsprung Disease is Illuminated by Comparative Analysis of the RET Protein Sequence", PNAS, vol. 102, No. 25, Jun. 21, 2005, pp. 8949-8954.

Kelly et al., "Randomized Phase III Trial of Paclitaxel Plus Carboplatin Versus Vinorelbine Plus Cisplatin in the Treatment of Patients with Advanced Non-Small-Cell Lung Cancer: A Southwest Oncology Group Trial", Journal of Clinical Oncology, vol. 19, No. 13, Jul. 1, 2001, pp. 3210-3218.

Kim et al., "A Phase II Study of Irinotecan Plus Cisplatin for Patients with Advanced Stage IIIB or IV NSCLC Previously Treated With Nonplatinum-Based Chemotherapy," Cancer, vol. 107, pp. 799-805, 2006.

Kim et al., "An Orally Administered Multitarget Tyrosin Kinase Inhibitor, SU11248, is a Novel Potent Inhibitor of Thyroid Oncogenic RET/Papillary Thyroid Cancer Kinases", The Journal of Clinical Endocrinology & Metabolism, vol. 91, No. 10, 2006, pp. 4070-4076.

Lesueur et al., "Polymorphisms in RET and Its Coreceptors and Ligands as Genetic Modifiers of Multiple Endocrine Neoplasia Type 2A," Cancer Research, vol. 66, No. 2, pp. 1177-1180, Jan. 15, 2006.

Lin et al., "The Vascular Endothelial Growth Factor Receptor Tyrosine Kinase Inhibitor PTK787/ZK222584 Inhibits Growth and Migration of Multiple Myeloma Cells in the Bone Marrow Microenvironment," Cancer Research, vol. 62, pp. 5019-5026, Sep. 1, 2002.

Logie et al., "Activating Mutations of the Tyrosine Kinase Receptor FGFR3 Are Associated with Benign Skin Tumors in Mice and Humans", Human Molecular Genetics, vol. 14, No. 9, 2005, pp. 1153-1160.

Matsui et al., "E7080, a novel multi-targeted tyrosine kinase inhibitor, exhibits anti-angiogenic activity via inhibition of KIT signallling in a small cell lung cancer xenograft model," European Journal of Cancer, vol. 2, No. 8, 2004, p. 47, #146.

McCarty et al., "ZD6474, a Vascular Endothelial Growth Factor Receptor Tyrosine Kinase Inhibitor with Additional Activity Against Epidermal Growth Factor Receptor Tyrosine Kinase, Inhibits Orthotopic Growth and Angiogenesis of Gastric Cancer", Mol. Cancer Ther., vol. 3, No. 9, 2004, pp. 1041-1048.

McCulloch et al., "Astragalus-Based Chinese Herbs and Platinum-Based Chemotherapy for Advanced Non-Small-Cell Lung Cancer: Meta-Analysis of Randomized Trials", Journal of Clinical Oncology, vol. 24, No. 3, Jan. 20, 2006, pp. 419-430.

Miller et al., "Paclitaxel Plus Bevacizumab Versus Paclitaxel Alone for Metastatis Breast Cancer", New England Journal of Medicine, vol. 357, 2007, pp. 2666-2676.

Mologni et al., "Inhibition of RET Tyrosine Kinase of SU5416", Journal of Molecular Endocrinology, vol. 37, No. 2, 2006, pp. 199-212, XP003022512.

Morgan et al., "Dynamic Contrast-Enhanced Magnetic Resonance Imaging As a Biomarker for the Pharmacological Response of PTK787/ZK222584, an Inhibitor of the Vascular Endothelial Growth Factor Receptor Tyrosine Kinases . . . ," Journal of Clinical Oncology, vol. 21, No. 21, Nov. 1, 2003, pp. 3955-3964.

Morikawa et al., "Angiogenesis and Pericytes: Putative Positive Function of Pericytes in Angiogenesis," The Cell, vol. 37, No. 4, 2005, pp. 164-168.

Naski et al., "Graded Activation of Fibroblast Growth Factor Receptor 3 by Mutations Causing Achondroplasia and Thanatophoric Dysplasia", Nature Genetics, vol. 13, pp. 233-237, Jun. 1996.

Ohe et al., "Randomized phase III study of cisplatin plus irinotecan versus carboplatin plus paclitaxel, cisplatin plus gemcitabine, and cisplatin plus vinorelbine for advanced non-small-cell lung cancer . . . ," Annals of Oncology, vol. 18, pp. 317-323, 2007.

Olaso et al., "DDR2 Receptor Promotes MMP-2-Mediated Proliferation and Invasion by Hepatic Stellate Cells", The Journal of Clinical Investigation, vol. 108, No. 9, Nov. 2001, pp. 1369-1378.

Ozols et al., "Phase III Trial of Carboplatin and Paclitaxel Compared with Cisplatin and Paclitaxel in Patients with Optimally Resected Stage III Ovarian Cancer: A Gynecologic Oncology Group Study", Journal of Clinical Oncology, vol. 21, No. 17, Sep. 1, 2003, pp. 3194-3200.

Paterson et al., "Preclinical studies of fibroblast growth factor receptor 3 as a therapeutic target in multiple myeloma," British Journal of Haematology, vol. 124, pp. 595-603, 2004.

Plowright et al., "Ectopic expression of fibroblast growth factor receptor 3 promotes myeloma cell proliferation and prevents apoptosis," Blood, vol. 95, No. 3, pp. 992-998, Feb. 1, 2000.

Proceedings of the American Association for Cancer Research, Experimental and Molecular Therapeutics, vol. 47, Apr. 2006, p. 890.

Salmon et al., "Anti-Angiogenic Treatment of Gastrointestinal Malignancies," Cancer Investigation, vol. 23, pp. 712-726, 2005.

Sandler et al., "Phase III Trial Gemcitabine Plus Cisplatin Versus Cisplatin Alone in Patients with Locally Advanced or Metastatic Non-Small-Cell Lung Cancer", Journal of Clinical Oncology, vol. 18, No. 1, Jan. 2000, pp. 122-130.

Santoro et al., "Drug Insight: Small-Molecule Inhibitors of Protein Kinases in the Treatment of Thyroid Cancer", Nature Clinical Practice Endocrinology & Metabolism, vol. 2, No. 1, pp. 42-52, Jan. 2006.

Santoro et al., "Minireview: RET: Normal and Abnormal Functions", Endocrinology, vol. 145, No. 12, pp. 5448-5451, 2004.

Shiang et al., "Mutations in the Transmembrane Domain of FGFR3 Cause the Most Common Genetic Form of Dwarfism, Achondroplasia," Cell, vol. 78, pp. 335-342, Jul. 29, 1994.

Shimizu et al., "Orally active anti-proliferation agents: novel diphenylamine derivatives as FGF-R2 autophosphorylation inhibitors," Bioorganic & Medicinal Chemistry Letters, vol. 14, pp. 875-879, 2004.

Supplementary European Search Report for European Application No. 07743994.1 dated May 4, 2010.

Takahashi et al., "A case of inoperable scirrhous gastric cancer that responded remarkably to a combination of TS-1+Paclitaxel . . . ," Japanese Journal of Cancer Chemother., vol. 31, No. 7, Jul. 2004, pp. 1093-1095.

Tan et al., "Randomized Study of Vinorelbine-Gemcitabine Versus Vinorelbine-Carboplatin in Patients with Advanced Non-Small Cell Lung Cancer", Lung Cancer, vol. 49, No. 2, 2005, pp. 233-240.

Trudel et al., "CHIR-258, a novel, multitargeted tyrosine kinase inhibitor for the potential treatment of t(4;14) multiple myeloma," Blood, vol. 105, pp. 2941-2948, 2005.

Trudel et al., "Inhibition of fibroblast growth factor receptor 3 induces differentiation and apoptosis in t(4;14) myeloma," Blood, vol. 103, No. 9, pp. 3521-3528, May 1, 2004.

U.S. Notice of Allowance for U.S. Appl. No. 12/244,227, dated Oct. 22, 2010.

U.S. Office Action for U.S. Appl. No. 11/662,425, dated Sep. 28, 2010.

Ueda et al., "Deletion of the Carboxyl-Terminal Exons of K-sam/FGFR2 by Short Homology-mediated Recombination, Generating Preferential Expression of Specific Messenger RNAs," Cancer Research, vol. 59, pp. 6080-6086, Dec. 15, 1999.

US Office Action for U.S. Appl. No. 10/797,903, dated Aug. 20, 2009.

Van Oers et al., "A Simple and Fast Method for Simultaneous Detection of Nine Fibroblast Growth Factor Receptor 3 Mutations in Bladder Cancer and Voided Urine", Clinical Cancer Research, vol. 11, No. 21, Nov. 1, 2005, pp. 7743-7748.

Vogel et al., "Sensing extracellular matrix: An update on discoidin domain receptor function," Cellular Signalling, vol. 18, pp. 1108-1116, 2006.

Wakui, "Chemotherapy for Scirrhous Gastric Cancer", Jpn. J. Cancer Chemother., vol. 21, No. 14, Oct. 1994, pp. 2398-2406.

Wang et al., "Phase II study of gemcitabine and carboplatin in patients with advanced non-small-cell lung cancer," Cancer Chemother Pharmacol, vol. 60, pp. 601-607, 2007.

Werner et al., "Gastric Adenocarcinoma: Pathomorphology and Molecular Pathology", J. Cancer Res. Cllin. Oncol., vol. 127, 2001, pp. 207-216.

Willett et al., "Direct Evidence that the VEGF-Specific Antibody Bevacizumab has Antivascular Effects in Human Rectal Cancer", Nature Medicine, vol. 10, No. 2, Feb. 2004, pp. 145-147.

Wozniak et al., "Randomized Trial Comparing Cisplatin With Cisplatin Plus Vinorelbine in the Treatment of Advanced Non-Small-Cell Lung Cancer: A Southwest Oncology Group Study," Journal of Clinical Oncology, vol. 16, No. 7, Jul. 1998, pp. 2459-2465.

Yamada et al., "New Technique for Staining", Monthly Medical Technology Supplementary Volume.

Yanagihara et al., "Development and biological analysis of peritoneal metastatis mouse models for human scirrhous stomach cancer," Cancer Science, vol. 96, No. 6, pp. 323-332, Jun. 2005.

Zhu et al., "Fibroblast Growth Factor Receptor 3 Inhibition by Short Hairpin RNAs Leads to Apoptosis in Multiple Myeloma", Molecular Cancer Therapeutics, vol. 4, No. 5, 2005, pp. 878-798.

Zieger et al., "Role of Activating Fibroblast Growth Factor Receptor 3 Mutations in the Development of Bladder Tumors", Clinical Cancer Research, vol. 11, No. 21, Nov. 1, 2005, pp. 7709-7719.

Di Raimondo et al., "Angiogenic factors in multiple myeloma: higher levels in bone marrow than in peripheral blood," Haematologica, 2000, vol. 85, pp. 800-805.

Ocqueteau et al., "Expression of the CS117 antigen (C-Kit) on normal and myelomatous plasma cells," British Journal of Haematology, 1996, vol. 95, pp. 489-493.

Office Action in U.S. Appl. No. 12/094,492 mailed Mar. 24, 2011.

Anonymous, "Scientific Discussion," Internet Citation (http://www.ema.europa.eu/docs/en_GB/document_library/EPARScientific_Discussion/human/000406/WC500022203.pdf), Jan. 1, 2004, pp. 1/61-61/61.

Bastin, R. J. et al, "Salt Selection and Optimisation Procedures for Pharmaceutical New Chemical Entities," Organic Process Research and Development, Jan. 1, 2000, vol. 4, No. 5, pp. 427-435.

Berge, S.M. et al, "Pharmaceutical Salts," Journal of Pharmaceutical Sciences, Jan. 1, 1977, vol. 66, No. 1, pp. 1-19.

EPO Extended European Search Report, Appl. No. 06767145.3, May 23, 2011, pp. 1-7.

EPO Office Communication, Appl. No. 04807580.8, Apr. 18, 2011, pp. 1-9.

Gould, P. L., "Salt selection for basic drugs," International Journal of Pharmaceutics, Nov. 1, 1986, vol. 33, No. 1-3, pp. 201-217.

Morris, K. R. et al, "An intergrated approach to the selection of optimal salt form for a new drug candidate," International Journal of Pharmaceutics, May 9, 1994, vol. 105, No. 3, pp. 209-217.

Yu, L., "Amorphous pharmaceutical solids: preparation, characterization and stabilization," Advanced Drug Delivery Reviews, May 16, 2001, vol. 48, No. 1, pp. 27-42.

EPO Supplementary Search Report, Appl. No. 03791389.4, Jul. 7, 2011.

Paz, K. et al, "Development of Angiogenesis Inhibitors to Vascular Endothelial Growth Factor Receptor 2. Current Status and Future Perspective," Frontiers in Bioscience, May 1, 2005, vol. 10, pp. 1415-1439.

Pritzker, K.P.H., "Cancer Biomarkers: Easier Said Than Done," Clinical Chemistry, 2002, vol. 48, No. 8, pp. 1147-1150.

Tong, R.T. et al, "Vascular Normalization by Vascular Endothelial Growth Factor Receptor 2 Blockade Induces a Pressure Gradient Across the Vasculature and Improves Drug Penetration in Tumors," Cancer Research, Jun. 1, 2004, vol. 64, pp. 3731-3736.

USPTO Office Action, U.S. Appl. No. 11/997,543, May 19, 2011.

USPTO Office Action, U.S. Appl. No. 12/864,817, May 19, 2011.

Zhu, Z. et al, "Inhibition of human leukemia in an animal model with human antibodies directed against vascular endothelial growth factor receptor 2. Correlation between antibody affinity and biological activity," Leukemia, 2003, vol. 17, pp. 604-611.

* cited by examiner

UREA DERIVATIVE AND PROCESS FOR PREPARING THE SAME

This is a Divisional of application Ser. No. 10/577,308 filed on Apr. 28, 2006 now U.S. Pat. No. 7,683,172, and for which priority is claimed under 35 U.S.C. §120. Application Ser. No. 10/577,308 is the National Stage Application of PCT International Application No. PCT/JP2004/016526 filed on Nov. 8, 2004, which claims the benefit of priority of Japanese Application No. P2003-381249 filed on Nov. 11, 2003 under 35 U.S.C. §119. The contents of all of the aforementioned applications are incorporated herein by reference.

TECHNICAL FIELD

The present invention relates to urea derivatives which are effective for prevention or treatment of various diseases associated with abnormal angiogenesis, and to processes for preparing the same.

BACKGROUND ART

Urea derivatives represented by the general formula (C):

[Chemical Formula 1]

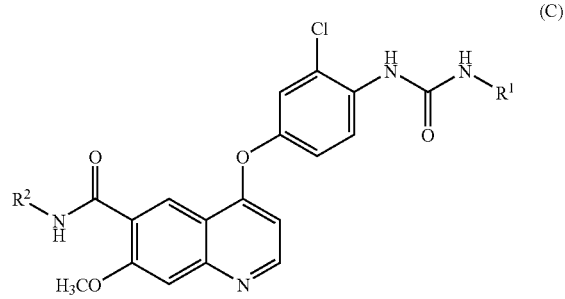

wherein $R^1$ represents hydrogen, $C_{1-6}$ alkyl or $C_{3-8}$ cycloalkyl, and $R^2$ represents hydrogen or methoxy, are known to exhibit excellent angiogenesis-inhibitory action (Patent document 1). Urea derivatives represented by general formula (C) also are known to exhibit powerful c-Kit kinase inhibitory action (Patent document 2, Non-patent document 1).

The preparing process described in Patent document 1 is useful as a process for preparing urea derivatives, but much room still remains for improvement in terms of total yield. It has therefore been desirable to develop an industrial process for preparing urea derivatives that gives a good total yield, as well as useful intermediates for such a preparing process.

Patent document 1 never discloses an efficient process for preparing urea compounds represented by the general formula (C), nor the useful intermediates represented by the general formulas (A-1) and (A-2), as according to the present invention.

Patent document 1: WO02/32872
Patent document 2: WO2004/080462
Non-patent document 1: 95th Annual Meeting Proceedings, AACR (American Association for Cancer Research), Volume 45, Page 1070-1071, 2004.

DISCLOSURE OF THE INVENTION

It is an object of the present invention to provide novel production intermediates of urea derivatives which are effective for prevention or treatment of various diseases associated with abnormal angiogenesis, as well as processes for their production.

As a result of much avid research in light of the circumstances described above, the present inventors discovered novel production intermediates of urea derivatives which are effective for prevention or treatment of various diseases associated with abnormal angiogenesis, as well as processes for their production, and have thereupon completed this invention. Specifically, the invention provides the following:

[1] A compound (A-1) or a salt thereof or a hydrate of the foregoing represented by the following formula:

[Chemical Formula 2]

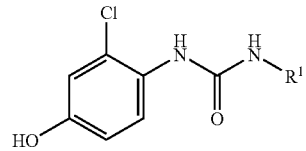

wherein $R^1$ represents hydrogen, $C_{1-6}$ alkyl or $C_{3-8}$ cycloalkyl.

[2] A compound or a salt thereof or a hydrate of the foregoing according to [1] wherein $R^1$ is hydrogen, methyl, ethyl, n-propyl or cyclopropyl;

[3] A compound or a salt thereof or a hydrate of the foregoing according to [1] wherein $R^1$ is cyclopropyl;

[4] A process for preparing a compound (A-1) represented by the following formula:

[Chemical Formula 6]

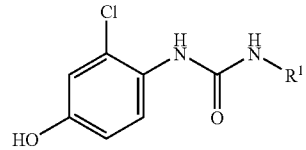

wherein $R^1$ has the same definition as above, characterized by reacting a compound (A-3) represented by the following formula:

[Chemical Formula 3]

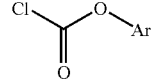

wherein Ar represents $C_{6-10}$ aryl optionally having 1 or 2 substituents selected from the group consisting of halogen, methyl, methoxy and nitro, with a compound (A-4) represented by the following formula:

[Chemical Formula 4]

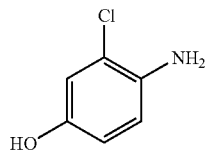
(A-4)

to afford a compound (A-2) represented by the following formula:

[Chemical Formula 5]

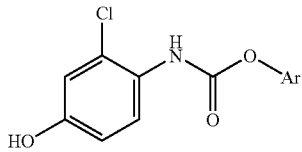
(A-2)

wherein Ar has the same definition as above, and then reacting the compound (A-2) with a compound represented by the formula $R_1$—$NH_2$, wherein $R^1$ has the same definition as above;

[5] A process according to [4], wherein $R^1$ is hydrogen, methyl, ethyl, n-propyl or cyclopropyl;

[6] A process according to [4], wherein $R^1$ is cyclopropyl;

[7] A process according to any one of [4] to [6], wherein Ar is phenyl;

[8] A compound (A-2) or a salt thereof or a hydrate of the foregoing represented by the following formula:

[Chemical Formula 7]

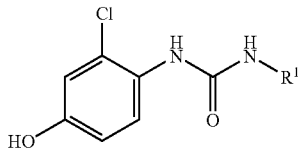
(A-1)

wherein Ar has the same definition as above;

[9] A compound or a salt thereof or a hydrate of the foregoing according to [8], wherein Ar is phenyl;

[10] A process for preparing compound (C) or a salt thereof represented by the following formula:

[Chemical Formula 10]

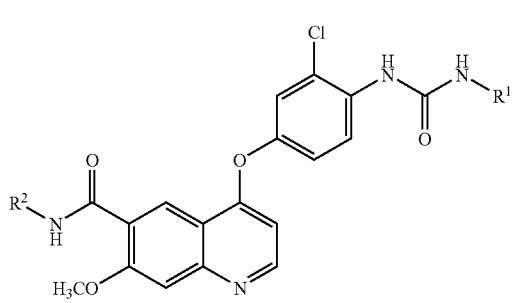
(C)

wherein $R^1$ and $R^2$ have the same definitions as above, characterized by reacting a compound (A-1) represented by the following formula:

[Chemical Formula 8]

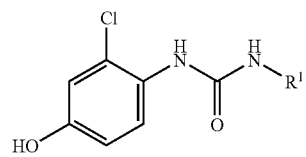
(A-1)

wherein $R^1$ has the same definition as above, with a compound (B) represented by the following formula:

[Chemical Formula 9]

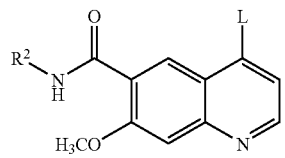
(B)

wherein $R^2$ represents hydrogen or methoxy, and L represents a leaving group;

[11] A process according to [10], characterized by using a base;

[12] A process according to [11], wherein the base is an alkali metal carbonate or an alkali metal alkoxide;

[13] A process according to [11], wherein the base is cesium carbonate, potassium carbonate or potassium t-butoxide;

[14] A process according to any one of [10] to [13], wherein $R^1$ is hydrogen, methyl, ethyl, n-propyl or cyclopropyl;

[15] A process according to any one of [10] to [13], wherein $R^1$ is cyclopropyl;

[16] A process according to any one of [10] to [15], wherein $R^2$ is hydrogen;

[17] A process according to any one of [10] to [16], wherein L is chlorine.

BEST MODE FOR CARRYING OUT THE INVENTION

The present invention will now be explained in detail, including explanations of the meanings of the terms and symbols used throughout the present specification.

The compounds or salts of the invention may be anhydrates, hydrates or solvates.

The term "$C_{1-6}$ alkyl" as used throughout the present specification refers to a monovalent group derived by removing any hydrogen atom from a C1-6 aliphatic hydrocarbon. It is a C1-6 straight- or branched-chain alkyl group, and as specific examples there may be mentioned methyl, ethyl, n-propyl, isopropyl, n-butyl, isobutyl, sec-butyl, tert-butyl, n-pentyl, isopentyl, sec-pentyl, neopentyl, 1-methylbutyl, 2-methylbutyl, 1,1-dimethylpropyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, among which methyl, ethyl and n-propyl are preferred.

The term "$C_{3-8}$ cycloalkyl" as used throughout the present specification refers to a C3-8 cyclic aliphatic hydrocarbon group, and as specific examples there may be mentioned cyclopropyl, cyclobutyl, cyclopentyl, cyclohexyl, cycloheptyl and cyclooctyl, among which cyclopropyl is preferred.

The term "$C_{6-10}$ aryl" as used throughout the present specification refers to a C6-10 aromatic hydrocarbon ring group, and as specific examples there may be mentioned phenyl, 1-naphthyl and 2-naphthyl, among which phenyl is preferred.

The term "halogen" as used throughout the present specification refers to fluorine, chlorine, bromine or iodine, among which chlorine is preferred.

The term "base" as used throughout the present specification refers to an organic base (for example, pyridine, 2,6-lutidine, collidine, triethylamine, diisopropylethylamine, diazabicyclo[5.4.0]undec-7-ene, etc.) or an inorganic base (an alkali metal carbonate (for example, cesium carbonate, potassium carbonate, sodium carbonate, etc.), an alkali metal alkoxide (for example, potassium t-butoxide, sodium ethoxide, etc.), an alkali metal hydride (for example, potassium hydride, sodium hydride, etc.), or an alkali metal hydroxide (for example, potassium hydroxide, sodium hydroxide, etc.). The base used in the step of reacting a compound (A-1) with a compound (B) to afford compound (C) is preferably an alkali metal carbonate or an alkali metal alkoxide, and more preferably cesium carbonate, potassium carbonate or potassium t-butoxide.

As examples of "salts" referred to throughout the present specification there may be mentioned inorganic acid salts, organic acid salts, inorganic base salts, organic base salts, and acidic or basic amino acid salts.

As preferred examples of inorganic acid salts there may be mentioned salts with hydrochloric acid, hydrobromic acid, sulfuric acid, nitric acid and phosphoric acid, and as preferred examples of organic acid salts there may be mentioned salts with acetic acid, succinic acid, fumaric acid, maleic acid, tartaric acid, citric acid, lactic acid, stearic acid, benzoic acid, methanesulfonic acid, ethanesulfonic acid and p-toluenesulfonic acid.

As preferred examples of inorganic base salts there may be mentioned alkali metal salts such as sodium salts and potassium salts, alkaline earth metal salts such as calcium salts and magnesium salts, and aluminum salts or ammonium salts. As preferred examples of organic base salts there may be mentioned salts with diethylamine, diethanolamine, meglumine and N,N-dibenzylethylenediamine.

As preferred examples of acidic amino acid salts there may be mentioned salts with aspartic acid and glutamic acid, and as preferred examples of basic amino acid salts there may be mentioned salts with arginine, lysine and ornithine.

The term "leaving group" as used throughout the present specification may be any group which is usually known as a leaving group in organic synthesis, without any particular restrictions, and as specific examples there may be mentioned halogens such as chlorine, bromine and iodine, alkylsulfonyloxy groups such as methanesulfonyloxy, trifluoromethanesulfonyloxy and ethanesulfonyloxy, arylsulfonyloxy groups such as benzenesulfonyloxy and p-toluenesulfonyloxy, alkoxy groups such as methoxy and ethoxy, and alkylthio groups such as methylthio and ethylthio. Preferred "leaving groups" are halogens such as chlorine, bromine and iodine, with chlorine being especially preferred.

Preparing processes according to the invention will now be explained in detail.

Preparing Process 1, Process for Preparing Urea (A-1)

[Chemical Formula 11]

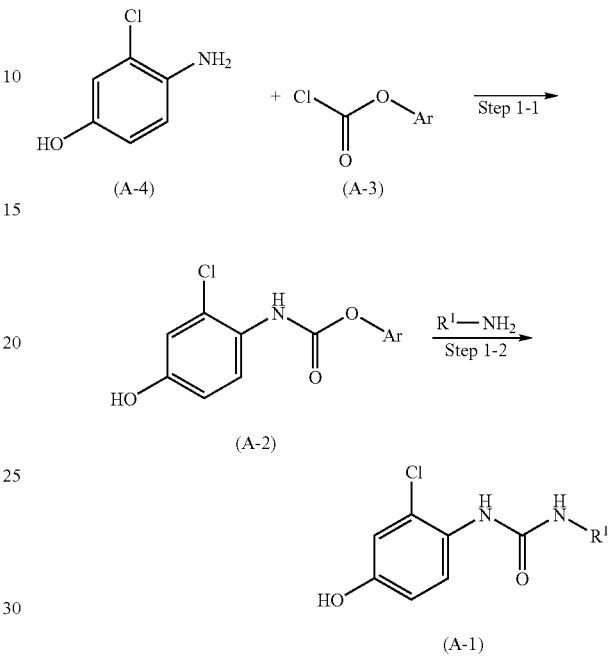

wherein the symbols have the same definitions as above.

[Step 1-1]

This is a step of reacting a carbamating reagent (A-3) such as phenyl chloroformate with a compound (A-4) to afford a compound (A-2). The reaction solvent used may be dimethylsulfoxide, N,N-dimethylformamide, N,N-dimethylacetamide, tetrahydrofuran, ethyl acetate or the like. The reaction may also utilize a base such as pyridine. The carbamating reagent (A-3) is used at 1-2 equivalents with respect to the compound (A-4). The base is used at 1-4 equivalents with respect to the compound (A-4). The reaction time is from 10 minutes to 30 hours. The reaction temperature is from 0° C. to heated reflux temperature, and is preferably between 0° C. and room temperature.

[Step 1-2]

This is a step of reacting an amine derivative $R_1$—$NH_2$ with the compound (A-2) to afford a compound (A-1). The reaction solvent used may be dimethylsulfoxide, N,N-dimethylformamide, N,N-dimethylacetamide, tetrahydrofuran, ethyl acetate, acetonitrile, toluene, chloroform or the like. The reaction may also utilize an organic base (for example, pyridine, triethylamine, diisopropylethylamine, etc.) or inorganic base (an alkali metal carbonate (for example, cesium carbonate, potassium carbonate, sodium carbonate, etc.) or an alkali metal hydride (for example, potassium hydride, sodium hydride, etc.)). The amine derivative is used at 1-3 equivalents with respect to the compound (A-2). The base is used at 1-3 equivalents with respect to the compound (A-2). The reaction time is from 10 minutes to 30 hours. The reaction temperature is from 0° C. to heated reflux temperature, and is preferably between 0° C. and room temperature.

Preparing Process 2, Process for Preparing Compound (C)

[Chemical Formula 12]

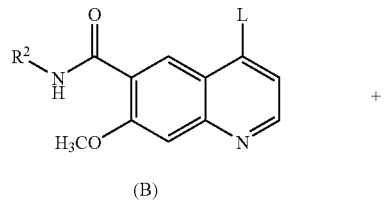

(B)

+

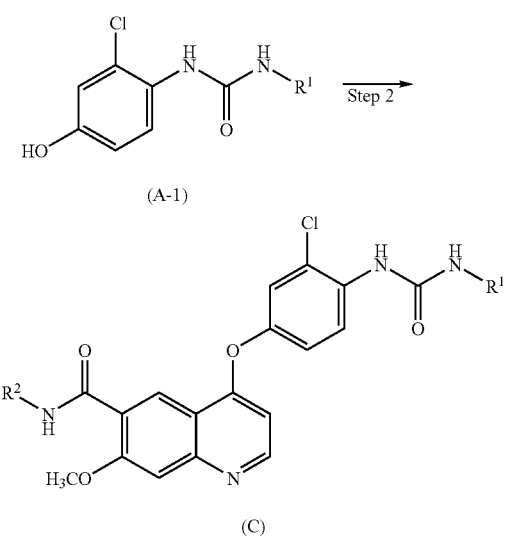

wherein the symbols have the same definitions as above.

[Step 2]

This is a step of reacting a compound (A-1) with a compound (B) to afford a compound (C). The reaction solvent used may be 1-methylpyrrolidone, dimethylsulfoxide, N,N-dimethylformamide, N,N-dimethylacetamide, 1,3-dimethyl-2-imidazolidinone, toluene, chlorobenzene or the like. As appropriate bases there may be added an organic base (for example, pyridine, 2,6-lutidine, collidine, triethylamine, diisopropylethylamine, diazabicyclo[5.4.0]undec-7-ene, etc.) or an inorganic base (an alkali metal carbonate (for example, cesium carbonate, potassium carbonate, sodium carbonate, etc.), an alkali metal alkoxide (for example, potassium t-butoxide, sodium ethoxide, etc.), an alkali metal hydride (for example, potassium hydride, sodium hydride, etc.), or an alkali metal hydroxide (for example, potassium hydroxide, sodium hydroxide, etc)). As such bases there are preferred alkali metal carbonates and alkali metal alkoxides, among which cesium carbonate, potassium carbonate and potassium t-butoxide are especially preferred. The compound (A-1) is used at 1-2 equivalents with respect to the compound (B). The base is used at 1-2 equivalents with respect to the compound (B). The reaction time is from 10 minutes to 48 hours. The reaction temperature is from room temperature to heated reflux temperature, and is preferably between 40° C. and 80° C.

Upon completion of the reaction, purification may be performed if necessary by an ordinary treatment method, for example, column chromatography using silica gel or an adsorption resin, or by recrystallization from an appropriate solvent.

EXAMPLES

Examples will now be described to facilitate understanding of the invention, but the invention is not limited to these examples.

Example 1

Phenyl N-(2-chloro-4-hydroxyphenyl)carbamate

[Chemical Formula 13]

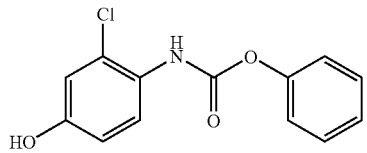

After suspending 4-amino-3-chlorophenol (23.7 g) in N,N-dimethylformamide (100 mL) and adding pyridine (23.4 mL) while cooling on ice, phenyl chloroformate (23.2 ml) was added dropwise below 20° C. Stirring was performed at room temperature for 30 minutes, and then water (400 mL), ethyl acetate (300 mL) and 6N HCl (48 mL) were added, the mixture was stirred and the organic layer was separated. The organic layer was washed twice with 10% brine (200 mL), and dried over magnesium sulfate. The solvent was removed to give 46 g of the title compound as a solid.

$^1$H-NMR (CDCl$_3$): 5.12 (1h, br s), 6.75 (1H, dd, J=9.2, 2.8 Hz), 6.92 (1H, d, J=2.8 Hz), 7.18-7.28 (4H, m), 7.37-7.43 (2H, m), 7.94 (1H, br s)

Example 2

1-(2-chloro-4-hydroxyphenyl)-3-cyclopropylurea

[Chemical Formula 14]

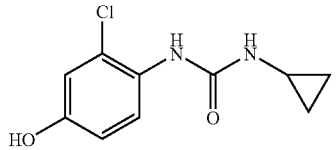

After dissolving phenyl N-(2-chloro-4-hydroxyphenyl) carbamate in N,N-dimethylformamide (100 mL), cyclopropylamine (22.7 mL) was added while cooling on ice and the mixture was stirred overnight at room temperature. Water (400 mL), ethyl acetate (300 mL) and 6N HCl (55 mL) were then added, the mixture was stirred and the organic layer was separated. The organic layer was washed twice with 10% brine (200 mL), and dried over magnesium sulfate. Prism crystals obtained by concentrating the solvent were filtered and washed with heptane to give 22.8 g of the title compound (77% yield from 4-amino-3-chlorophenol).

$^1$H-NMR (CDCl$_3$): 0.72-0.77 (2H, m), 0.87-0.95 (2H, m), 2.60-2.65 (1H, m), 4.89 (1H, br s), 5.60 (1H, br s), 6.71 (1H, dd, J=8.8, 2.8 Hz), 6.88 (1H, d, J=2.8 Hz), 7.24-7.30 (1H, br s), 7.90 (1H, d, J=8.8H)

Example 3

4-(3-chloro-4-(cyclopropylaminocarbonyl)aminophenoxy)-7-methoxy-6-quinolinecarboxamide

[Chemical Formula 15]

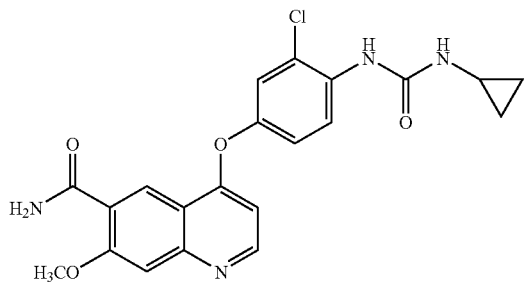

To dimethylsulfoxide (20 mL) were added 7-methoxy-4-chloro-quinoline-6-carboxamide (0.983 g), 1-(2-chloro-4-hydroxyphenyl)-3-cyclopropylurea (1.13 g) and cesium carbonate (2.71 g), followed by heating and stirring at 70° C. for 23 hours. After the reaction mixture was allowed to cool down to room temperature, water (50 mL) was added, and the produced crystals were collected by filtration to give 1.56 g of the title compound (88% yield).

$^1$H-NMR (d$_6$-DMSO): 0.41 (2H, m), 0.66 (2H, m), 2.56 (1H, m), 4.01 (3H, s), 6.51 (1H, d, J=5.6 Hz), 7.18 (1H, d, J=2.8 Hz), 7.23 (1H, dd, J=2.8, 8.8 Hz), 7.48 (1H, d, J=2.8 Hz), 7.50 (1H, s), 7.72 (1H, s), 7.84 (1H, s), 7.97 (1H, s), 8.25 (1H, d, J=8.8 Hz), 8.64 (1H, s), 8.65 (1H, d, J=5.6 Hz)

Example 4

4-(3-chloro-4-(cyclopropylaminocarbonyl)aminophenoxy)-7-methoxy-6-quinolinecarboxamide In a reaction vessel were placed 7-methoxy-4-chloro-quinoline-6-carboxamide (5.00 kg, 21.13 mol), dimethylsulfoxide (55.05 kg), 1-(2-chloro-4-hydroxyphenyl)-3-cyclopropylurea (5.75 kg, 25.35 mol) and potassium t-butoxide (2.85 kg, 25.35 mol) in that order, under a nitrogen atmosphere. After stirring at 20° C. for 30 minutes, the temperature was raised to 65° C. over a period of 2.5 hours. After stirring at the same temperature for 19 hours, 33% (v/v) acetone water (5.0 L) and water (10.0 L) were added dropwise over a period of 3.5 hours. Upon completion of the dropwise addition, the mixture was stirred at 60° C. for 2 hours, and 33% (v/v) acetone water (20.0 L) and water (40.0 L) were added dropwise at 55° C. or higher over a period of 1 hour. After then stirring at 40° C. for 16 hours, the precipitated crystals were collected by filtration using a nitrogen pressure filter, and the crystals were washed with 33% (v/v) acetone water (33.3 L), water (66.7 L) and acetone (50.0 L) in that order. The obtained crystals were dried at 60° C. for 22 hours using a conical vacuum drier to give 7.78 kg of the title compound (96.3% yield).

The processes for preparing urea derivatives according to the invention allow efficient production of urea derivatives, which are effective for prevention or treatment of various diseases associated with abnormal angiogenesis, by industrial preparing processes. The urea derivative intermediates according to the invention are useful as intermediates for efficient production of the aforementioned urea derivatives.

INDUSTRIAL APPLICABILITY

The processes for preparing urea derivatives according to the invention allow efficient production of urea derivatives, which are effective for prevention or treatment of various diseases associated with abnormal angiogenesis, by industrial preparing processes. The urea derivative intermediates according to the invention are useful as intermediates for efficient production of the aforementioned urea derivatives.

The invention claimed is:

1. A compound (A-1) or a salt thereof or a hydrate of the foregoing represented by the following formula:

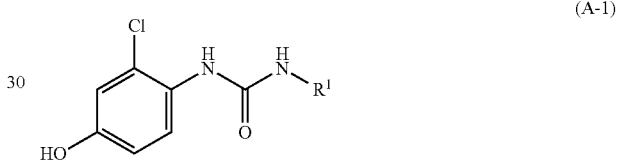

(A-1)

wherein R$^1$ represents hydrogen, C$_{1-6}$ alkyl or C$_{3-8}$ cycloalkyl.

2. A compound or a salt thereof or a hydrate of the foregoing according to claim 1, wherein R$^1$ is hydrogen, methyl, ethyl, n-propyl or cyclopropyl.

3. A compound or a salt thereof or a hydrate of the foregoing according to claim 1, wherein R$^1$ is cyclopropyl.

4. A compound (A-2) or a salt thereof or a hydrate of the foregoing represented by the following formula:

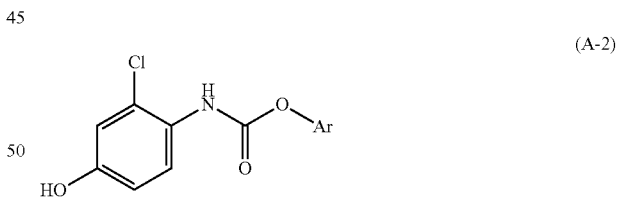

(A-2)

wherein Ar represents C$_{6-10}$ aryl optionally having 1 or 2 substituents selected from the group consisting of halogen, methyl, methoxy and nitro.

5. A compound or a salt thereof or a hydrate of the foregoing according to claim 4, wherein Ar is phenyl.

* * * * *